US005626759A

United States Patent [19]
Krantz et al.

[11] Patent Number: 5,626,759
[45] Date of Patent: May 6, 1997

[54] BLOOD TREATMENT DEVICE WITH MOVING MEMBRANE

[75] Inventors: William B. Krantz, Boulder, Colo.; Robert R. Bilodeau, Old Towne, Me.; Roger J. Elgas, Lakewood; Marc E. Voorhees, Arvada, both of Colo.

[73] Assignee: Regents of the University of Colorado, Boulder, Colo.

[21] Appl. No.: 284,057

[22] Filed: Aug. 1, 1994

[51] Int. Cl.$^6$ .............. A61M 1/14; B01D 61/00; C02F 1/44
[52] U.S. Cl. .............. 210/645; 210/321.67; 210/649; 422/46
[58] Field of Search .............. 422/46, 48; 210/321.4, 210/321.67, 645, 649; 128/DIG. 3; 95/46

[56] References Cited

U.S. PATENT DOCUMENTS

| | | | |
|---|---|---|---|
| 4,199,458 | 4/1980 | Nauman | 210/321 |
| 4,205,042 | 5/1980 | Lodbell et al. | 422/47 |
| 4,328,102 | 5/1982 | Bellhouse et al. | 210/321.4 |
| 4,357,239 | 11/1982 | Bellhouse et al. | 210/321.4 |
| 4,451,562 | 5/1984 | Elgas et al. | 435/48 |
| 4,455,230 | 6/1984 | Elgas et al. | 210/232 |
| 4,599,093 | 7/1986 | Steg, Jr. | 55/16 |
| 4,663,125 | 5/1987 | Gordon et al. | 422/48 |
| 4,818,490 | 4/1989 | Carson et al. | 422/46 |
| 5,316,724 | 5/1994 | Mathewson et al. | 422/48 |

OTHER PUBLICATIONS

Belhouse, B.J., "A High–Efficiency Membrane Oxygenator", Plastics in Medicine and Surgery, Sep., 1975, Conference in Glasgow, pp. 18.1–18.8.

Dorson et al., "Correlation of Pulsed Flow Vortex Shedding", Trans. Amer. Soc. Artif. Int. Organs, 1975, vol. XXI, pp. 335–341.

Drinker et al., "Practical Application of Secondary Flows in Membrane Oxygenators", Artificial Lungs for Acute Respiratory Failure, Theory and Practice, Academic Press, 1976, pp. 69–85.

Drinker, P.A., Ph.D., "Progress in Membrane Oxygenator Design", Anesthesiology, vol. 37, No. 2, Aug., 1972, pp. 242–260.

Driscoll et al., "A High Efficiency Artificial Lung Based on Vortex Shedding and an Ultrathin, Non–Porous Membrane", Arthur D. Little, Inc., pp. 1–23.

DuBois et al., "Hemocompatibility of the Interpulse Membrane Oxygenator During Prolonged Veno–Venous Perfusion in Sheep", asaio Journal, Oct./Dec., 1984, vol. 7, pp. 146–150.

Egan, et al., "Gas Transfer Characteristics of the Interpulse Membrane Oxygenator During Prolonged Veno–Venous Perfusion in Sheep", asaio Journal, Oct./Dec. 1984, vol. 7, pp. 151–154.

Hooper, F.C., "The Effect of Vibration of the Boundary Wall on Liquid–To–Surface Heat Transfer", Univ. of Toronto, Technical Publication Series, Oct., 1964, TP 6408.

Kitrilakis et al., "A Rotating Disk Membrane Oxygenator", Artificial Lungs for Acute Respiratory Failure, Theory and Practice, Academic Press, 1976, pp. 211–221.

(List continued on next page.)

*Primary Examiner*—Nina Bhat
*Attorney, Agent, or Firm*—Sheridan Ross P.C.

[57] ABSTRACT

A medical device and method for affecting mass transfer between blood and a fluid. In one application, this mass transfer is an oxygenation of the blood. Generally, a membrane which separates the blood and fluid is moved in a predetermined manner and in a direction which is substantially parallel to that of the primary direction of the flow to augment the mass transfer efficiency/rate. Importantly, this movement of the membrane is relative to the blood mass transfer boundary layer which steepens or increases the oxygen concentration gradient and decreases the thickness of the blood mass transfer boundary layer and thereby improves upon the mass transfer efficiency/rate of oxygen into the blood.

40 Claims, 12 Drawing Sheets

OTHER PUBLICATIONS

Nelems et al., "Prolonged Pulmonary Support of New-Born Lams with the Oxford Membrane Oxygenator", Trans, Amer, Sco. Artif. Int. Organs, 1974, vol. XX, pp. 293–298.

Spratt et al., "Design and Performance of High Efficiency Pulsatile Membrane Lung", Revision Nov. 1, 1976.

Takahashi et al., "A New Correlation Method for the Effect of Vibration on Forced-Convection Heat Transfer", Journal of Chemical Engineering of Japan, vol. 23, No. 1, 1990, pp. 45–49.

Voorhees, M.E., "Oxygenator Technology: The Future", Perfusion 1994:9: pp. 191–194.

Voorhees et al., "Membrane and Bubble Oxygenators", Techniques in Extracorporeal Circulation, 3rd Edition, pp. 42–55, published 1992.

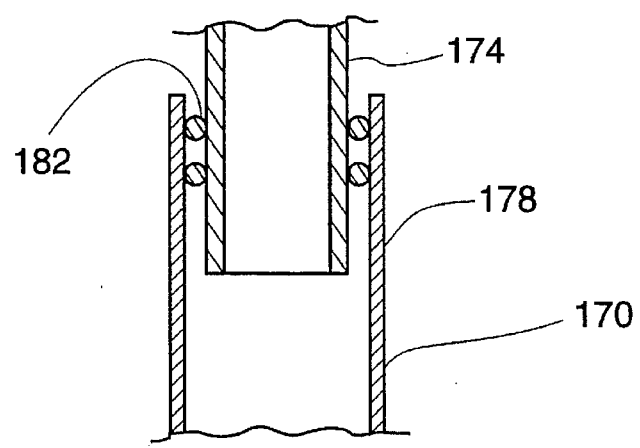
Fig. 1A
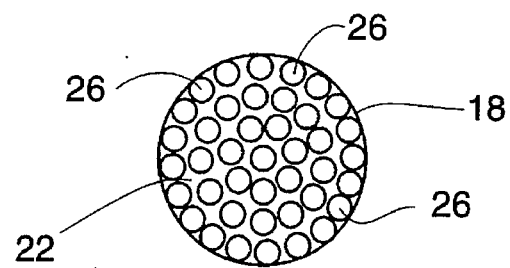
Fig. 2
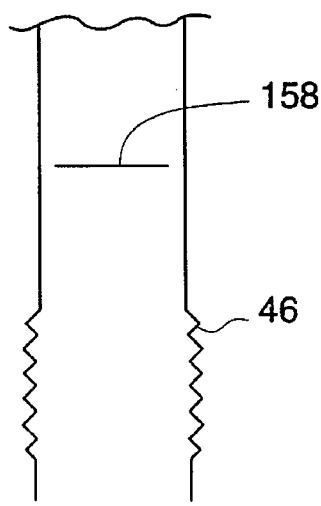 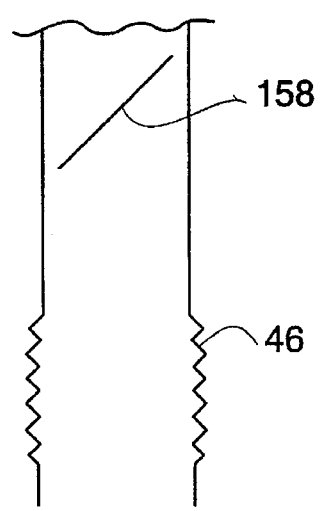 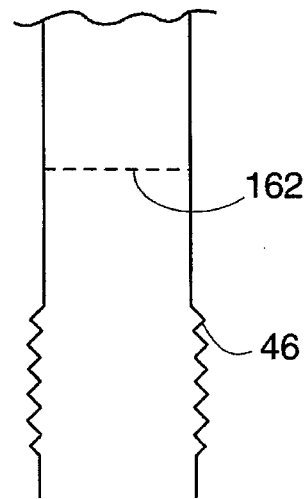
Fig. 4A          Fig. 4B          Fig. 4C NOTE: Mass-transfer data showing the effect of vibrational penetration depth on the ratio of the Sherwood number with vibrations to the Sherwood number without vibrations for a constant value of the vibrational velocity group, $\frac{A\omega}{v} = 8.5$. The 95% confidence level equals $\pm 0.037$.

NOTE: Mass-transfer data showing the effect of vibrational penetration depth on the ratio of the Sherwood number with vibrations to the Sherwood number without vibrations for a constant value of the vibrational velocity group, $\frac{A\omega}{v} = 12$. The 95% confidence level equals $\pm 0.037$.

NOTE: Mass-transfer data showing the effect of vibrational penetration depth on the ratio of the Sherwood number with vibrations to the Sherwood number without vibrations for a constant value of the vibrational velocity group, $\frac{A\omega}{v}$ =16.5. The 95% confidence level equals ± 0.044.

NOTE: Mass-transfer data showing the effect of vibrational velocity on the ratio of the Sherwood number with vibrations to the Sherwood number without vibrations for a constant vibrational penetration depth, $\frac{\omega R^2}{v} = 20$. This value of $\frac{\omega R^2}{v}$ corresponds to $f = 6\ Hz$.
The 95% confidence level equals ± 0.037.

NOTE: Mass-transfer data showing the effect of vibrational velocity on the ratio of the Sherwood number with vibrations to the Sherwood number without vibrations for a constant vibrational penetration depth, $\omega R^2/\nu = 27$. This value of $\omega R^2/\nu$ corresponds to $f = 8\ Hz$.
The 95% confidence level equals ± 0.037.

NOTE: Mass-transfer data showing the effect of vibrational velocity on the ratio of the Sherwood number with vibrations to the Sherwood number without vibrations for a constant vibrational penetration depth, $\frac{\omega R^2}{\nu} = 34$. This value of $\frac{\omega R^2}{\nu}$ corresponds to $f = 10\ Hz$.
The 95% confidence level equals $\pm 0.037$.

NOTE: Mass-transfer data showing the effect of vibrational velocity on the ratio of the Sherwood number with vibrations to the Sherwood number without vibrations for a constant vibrational penetration depth, $\frac{\omega R^2}{\nu} = 41$. This value of $\frac{\omega R^2}{\nu}$ corresponds to $f = 12\ Hz$.
The 95% confidence level equals ± 0.037.

NOTE: Mass-transfer data showing the effect of vibrational velocity on the ratio of the Sherwood number with vibrations to the Sherwood number without vibrations for a constant vibrational penetration depth, $\omega R^2/v = 51$. This value of $\omega R^2/v$ corresponds to $f = 15\ Hz$.
The 95% confidence level equals $\pm 0.037$.

BLOOD TREATMENT DEVICE WITH MOVING MEMBRANE

FIELD OF THE INVENTION

The present invention generally relates to augmenting mass transfer through a membrane by moving the membrane relative to fluid substantially adjacent to the membrane, and in one particular application to augmenting mass transfer between blood and a fluid such as in oxygenation, dialysis, and plasma separation applications.

BACKGROUND OF THE INVENTION

A variety of blood treatment applications involve mass transfer. For instance, extracorporeal oxygenators are used by patients undergoing cardiopulmonary bypass procedures for cardiac surgery and by adult and infant patients with respiratory problems to oxygenate the blood and remove carbon dioxide therefrom. One type of extracorporeal oxygenator which has become relatively successful is the membrane oxygenator. Generally, in these types of oxygenators a flow of blood and a source of oxygen are separated by a semi-permeable membrane which allows the oxygen to diffuse into the blood and which also allows carbon dioxide within the blood to diffuse into the oxygen source.

There are two primary factors which affect the mass transfer rate in a membrane oxygenator or more specifically which provide resistance to the desired mass transfer, namely the diffusion resistance of the membrane material itself and the diffusion resistance of the blood (there is also a mass transfer boundary layer resistance to the transfer of carbon dioxide out of the blood which may be on the blood and/or gas side). Significant advances have been made in the development of suitable membrane materials with low diffusion resistance, and comparatively the diffusion resistance of the blood adjacent to the membrane is in fact significantly greater than the membrane diffusion resistance. This is true regardless of the configuration of the membrane (e.g., whether of a tubular, flat sheet, or pleated sheet configuration). In extracorporeal membrane oxygenators, this blood diffusion resistance is significantly more than in the natural capillaries of a human being since the size of the oxygenator blood channels is significantly greater than the size of the natural capillaries. Therefore, reducing the diffusion resistance of the blood, or more particularly the resistance provided by the mass transfer boundary layer of blood adjacent the membrane, has been the object of significant development efforts in membrane oxygenator design.

Passive augmentation techniques have been investigated for reducing the mass transfer boundary layer resistance and thus increasing the mass transfer rate in membrane oxygenators. Generally, passive augmentation utilizes the energy of the flow of the blood to induce secondary flows or eddy-type currents adjacent the membrane in order to reduce the resistance to mass transfer. More specifically, the membrane is configured such that blood flowing thereby is effectively forced to mix with more interiorly positioned portions of the blood flow. For instance, the membrane may be furrowed or a mesh may be positioned adjacent a substantially smooth membrane surface to induce an eddy-type mixing. Moreover, an eddy-like secondary flow may also be induced by utilizing a coiled tube configuration as the blood-receiving membrane in which case the curvature of the coiled tube produces the noted secondary flows.

Active augmentation techniques have also been investigated for reducing the mass transfer resistance and thus increasing the mass transfer rate in membrane oxygenators. Generally, active augmentation differs from passive augmentation in that external energy is applied in some manner to the oxygenating system. One type of active augmentation technique which has been used in some oxygenators is a pulsing of the flow of blood past a stationary membrane. In this case, a substantial portion of the energy applied to the system is concentrated on the interior portions of the blood flow (i.e., pulsing the blood flow does not concentrate the energy at the mass transfer boundary layer). Other active augmentation techniques which have been used at least experimentally are rotating membrane disk oxygenators in which a flow of blood is directed onto the face of a rotating membrane disk (i.e., the membrane surface is positioned perpendicularly to the blood flow), as well as oscillating torroid oxygenators in which oscillations of, for instance, the above-described coiled tube configuration are provided to further enhance the noted secondary flows.

Other blood treatment applications also utilize mass transfer principles. These include dialysis where a dialyzer includes a number of small tubes within a housing. Blood typically flows through the tubes and a typically liquid dialysate is contained within the housing and surrounds the tubes. As a result, impurities and excess fluid flow from the blood through the membrane and into the dialysate. Ultra-filters or blood concentrators utilize similar principles in removing excess fluid from the blood for concentrating the same.

SUMMARY OF THE INVENTION

One application of the present invention relates to a medical device for affecting mass transfer between blood and a fluid. For instance, one particularly desirable application of the present invention is in an oxygenator which utilizes movement of a membrane separating a typically substantially laminar flow of blood (e.g., a Reynolds number of less than about 2000) from an oxygen source to provide for a desired mass transfer rate. As a result of the particular type of movement utilized by the present invention in this application, namely a relative movement between the membrane and the blood mass transfer boundary layer (which is located substantially adjacent the membrane) in a direction which is substantially parallel with the primary direction of the flow, the mass transfer resistance of the blood mass transfer boundary layer or film is desirably reduced. This type of relative movement may also reduce the potential for fouling of the membrane.

In the noted blood treatment application, the present invention is embodied within a medical device for affecting mass transfer between blood and a fluid (e.g., oxygen, dialysate). Generally, the device includes a first conduit for receiving a flow of blood and is formed at least in part from a membrane which separates the flow of blood from the fluid, or more typically a flow of such fluid. The membrane may assume a variety of configurations. For instance, the membrane may be a tube or a tube bundle of a plurality of spaced tubes and the fluid may be contained within a second conduit which is positioned about the first conduit. Moreover, the membrane may be a planar or pleated sheet or sheets which at least in part define one or more blood channels. Nonetheless, in order to effect the desired mass transfer, the membrane is permeable with respect to at least one component of at least one of the blood and the fluid (e.g., there may be a mass transfer to and/or from the blood, such as a transfer of oxygen to the blood and a transfer of carbon dioxide from the blood in a blood oxygenator application of the present invention).

When a flow of blood and fluid is provided, at least one mass transfer boundary layer exists adjacent to the membrane which provides a resistance to mass transfer between the blood and the fluid (e.g., in an oxygenator application the blood mass transfer boundary layer provides the primary resistance, whereas in a dialysis application the resistance of the blood mass transfer boundary layer and the dialysate mass transfer boundary layer provide about equal resistance). The present invention utilizes movement of the membrane relative to the flow thereby, more specifically the mass transfer boundary layer(s), in order to reduce this resistance. Generally, this relative movement between the membrane and mass transfer boundary layer(s) steepens or increases the concentration gradient and thereby improves the mass transfer rate.

The relative movement required by the present invention may be realized by interconnecting the first conduit with the remainder of the system with one or more particular types of connectors. For instance, the above-described device may further include input and output lines which are each interconnected with the first conduit by variable volume or variable length connectors such as a bellows or a telescoping-like connector. In such a case, the input and output lines may remain substantially stationary while the entire first conduit and thus the membrane is moved in accordance with principles of the present invention. That is, these types of connectors move between expanded or extended (e.g., larger volume, longer) and contracted or retracted (e.g., smaller volume, shorter) conditions/positions. This allows the membrane to move relative to the mass transfer boundary layer(s). Moreover, when the first conduit is being moved in a direction generally away from its outlet side, the movement of the connector (e.g., via a lengthening of the same) on the outlet side of the first conduit also accommodates for what is effectively an instantaneous increase in the flow out of the first conduit (compared to the first conduit being in a stationary position). Although the use of two of the noted types of connectors has been described herein, it may be possible to achieve the desired degree of relative movement utilizing only one of the connectors (e.g., having such a connector on only the inlet or outlet side).

The type of relative movement in accordance with principles of the present invention is subject to additional characterizations. Initially, one type of movement which may provide the noted relative movement is an axial advancement of an axially extending first conduit (e.g., an axial advancement which is parallel to a uniform flow which is defined as a flow wherein the velocity does not change from point to point along any of the streamlines in the flow field, such that the streamlines are straight and parallel), although other membrane configurations may be suited for this axial advancement. Moreover, movement of the first conduit which produces the noted relative movement may be in a direction which is substantially parallel with the streamlines which define the flow pattern through the first conduit (e.g., an axial advancement may be used for a first conduit which is only generally axially extending and meanders to a degree such that the streamlines which define the flow field are not straight but curve to a limited degree).

With further regard to characterizations of relative membrane movement in accordance with the present inventions the type of movement of the membrane relative to the mass transfer boundary layer(s) may be characterized by the types of forces which are generated. For instance, the movement itself may be that which generates substantially only a shear-like force between the first conduit and the mass transfer boundary layer(s). In addition, the movement may be that which creates a force between the membrane and the mass transfer boundary layer(s), and such that the primary component of all force vectors which define the force at any one location are all substantially parallel with the primary direction of at least one of the flows.

The movement of the membrane relative to the mass transfer boundary layer(s) according to the present invention may be further characterized as being a periodic-like motion. Moreover, the movement may be a reciprocation of the first conduit back and forth between two positions (e.g., substantially along an axis). The movement may be substantially symmetrical (i.e., through use of a sine wave signal), or may be asymmetrical (i.e., using a saw tooth wave signal). Furthermore, the movement of the membrane may include one or more pauses. For instance, in moving the membrane between two extreme positions, there may be a pause at one or both of these positions and/or at an intermediate position, such that the membrane is intermittently maintained in a substantially stationary position. In addition, the wave form, amplitude and/or frequency which control such movements may be selected/adjusted in order to accommodate the oxygenation needs, and thus provide a desired degree of control over the mass transfer rate.

The above-described medical device may include additional features for further augmenting the mass transfer rate. For instance, one or more passive augmentation techniques such as those discussed above may be incorporated into the present invention (e.g., furrowed membranes, the use of mesh adjacent a smooth membrane surface, a coiled tube). Furthermore, the flow of blood through the first conduit membrane may be pulsed and/or secondary flows may be utilized. Moreover, a counterflow of blood may be established. In this regard, a partial dam-like structure or flow impediment may be positioned near the inlet to and/or outlet from the first conduit (typically upstream/downstream of the first conduit) and in the flow path of the blood to exert an accelerating-like or decelerating-like force on the flow of blood through the first conduit as a result of movement in accordance with principles of the present invention (e.g., utilizing momentary reductions in fluid velocity to further enhance relative movement between the membrane and the mass transfer boundary layer (s)).

In order to illustrate the above, assume a substantially axially extending first conduit which is reciprocated between first and second positions and in which the flow of blood is generally in the direction of the second position. In this case, when the first conduit is moved from the first position to the second position, the forward velocity of a portion of the flow of blood through the first conduit is momentarily reduced due to the partial dam-like structure or flow impediment positioned on the outlet side of the first conduit. That is, movement of the first conduit towards the second position creates a pressure increase on the end of the first conduit proximate the second position, which momentarily reduces the forward velocity of a portion of the flow of blood. Similarly, when the first conduit is moved from the second position back toward the first position, a partial dam-like structure or flow impediment positioned on the inlet side of the first conduit will exert a force on the blood within the first conduit and force the same toward the outlet of the first conduit,

BRIEF DESCRIPTION OF THE DRAWINGS

FIG. 1A illustrates an alternative for interconnecting the oxygenator into the system of FIG. 1;

FIG. 2 is a cross-sectional view of the oxygenator of FIG. 1 taken along lines 2—2;

FIGS. 4A–C are general views of various flow impediments which may be used to generate a pressure pulse and/or counterflow of blood through the oxygenator of FIG. 1;

DETAILED DESCRIPTION

The present invention will be described with reference to the accompanying drawings which assist in illustrating its various features. Broadly, the present invention is a method and apparatus for augmenting the mass transfer rate between two fluids by moving an intermediate membrane relative to the mass transfer boundary layer associated with at least one of the fluids. This movement reduces the diffusion resistance of this boundary layer. The principles of the present invention to be discussed herein are applicable to a variety of applications, including blood treatment such as dialysis, ultrafiltration or blood concentration. Moreover, the present invention may be implemented into membrane blood oxygenators for enhancing the mass transfer of oxygen into the blood. The present invention will be described with regard to this particular application. Specifically, the present invention will be described in relation to a tubular membrane blood oxygenator, although blood oxygenators which utilize other membrane configurations such as a planar sheet(s) and/or a pleated sheet(s) to define one or more blood channels may also incorporate principles of the present invention.

Figure 1:
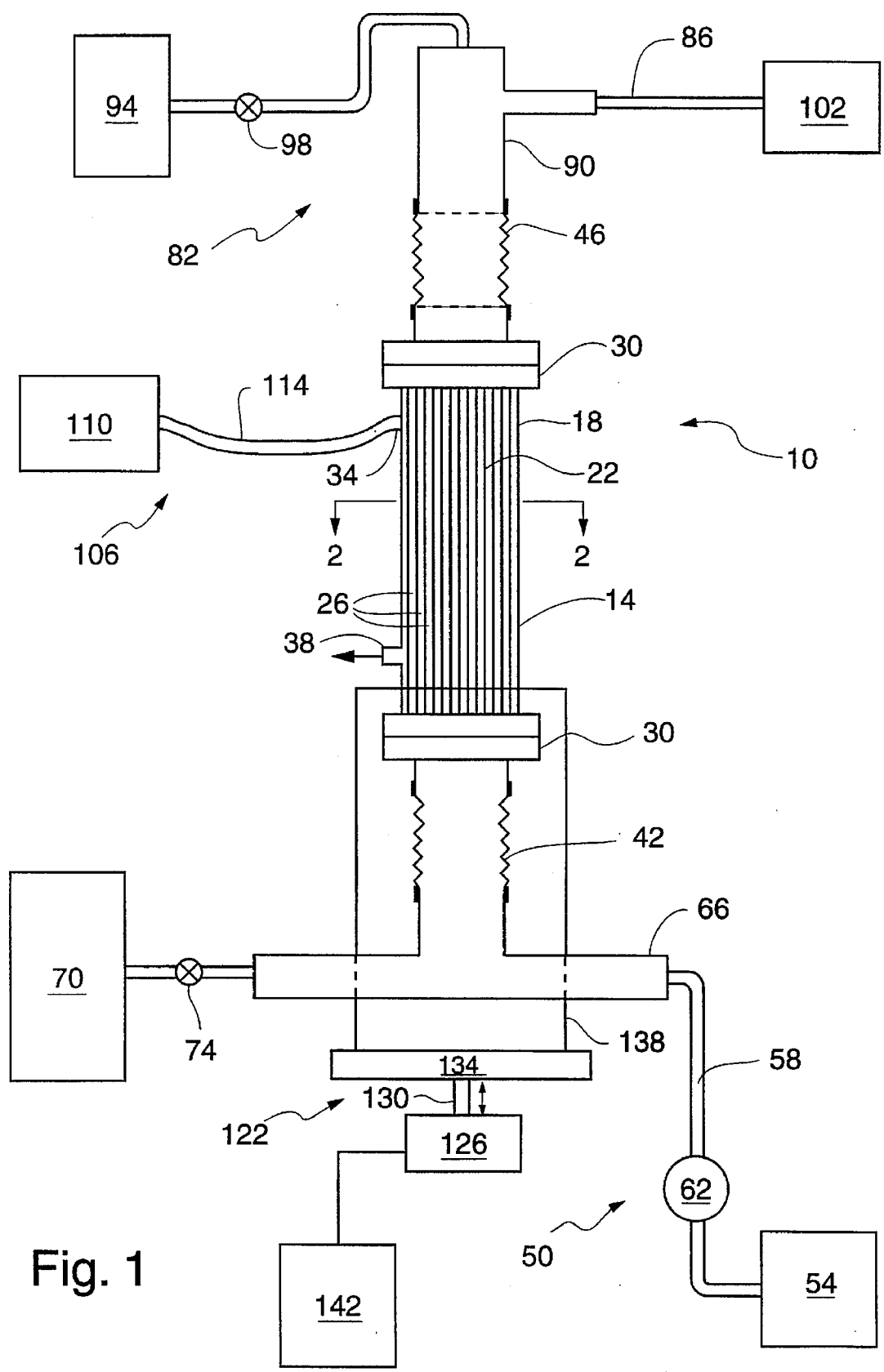
FIG. 1 is a schematic representation of an oxygenator system in accordance with principles of the present invention.

An oxygenator system 10 in accordance with principles of the present invention is illustrated in FIG. 1. The oxygenator system 10 generally includes a tubular membrane oxygenator 14, a blood supply assembly 50 and a blood discharge assembly 82 for providing oxygen-depleted blood to and removing oxygenated blood from the oxygenator 14, respectively, an oxygen supply assembly 106 for providing a source of oxygen for the desired mass transfer, and a drive assembly 122 for moving the oxygenator 14, more specifically its tubular membranes, relative to the flow of blood therethrough, and particularly relative to the blood mass transfer boundary layer adjacent the membrane wall, to augment the mass transfer rate.

The blood supply assembly 50 provides a preferably continuous flow of blood to the oxygenator 14 for oxygenation. In this regard, the blood supply assembly 50 includes a peristaltic pump 62 which pumps blood from a blood reservoir 54 through the oxygenator 14 via blood inlet tubing 58 and an appropriately configured inlet manifold 66. The inlet manifold 66 is interconnected with the oxygenator 14 by a variable volume and/or variable length connector such as an inlet bellows 42 which allows the oxygenator 14 to move relative to the preferably substantially stationary inlet manifold 66, and thereby to provide for effective relative movement between the oxygenator 14 and the flow of blood therethrough and specifically the blood mass transfer boundary layer. The blood supply assembly 50 further includes an inlet surge tank 70 which is also interconnected with the inlet manifold 66 and which allows the oxygenator system 10 to be operated in a manner which minimizes the generation of pressure pulses which can cause additional counterflows of blood through the oxygenator 14. In order to provide the operator with selective operation capabilities, however, a valve 74 is positioned between the inlet surge tank 70 and the inlet manifold 66 to allow for a blood pressure pulse/counterflow operating mode as well.

Oxygenated blood is removed from the oxygenator 14 by the blood discharge assembly 82. The blood discharge assembly 82 generally includes a blood receptacle 102 which is interconnected with the discharge side of the oxygenator 14 by an appropriately configured outlet manifold 90 and blood outlet tubing 86. The outlet manifold 90 is interconnected with the oxygenator 14 by a variable volume and/or variable length connector such as an outlet bellows 46 which allows the oxygenator 14 to move relative to the preferably substantially stationary outlet manifold 90, and thereby to provide for effective relative movement between the oxygenator 14 and the flow of blood therethrough and specifically the blood mass transfer boundary layer (e.g., the outlet bellows 46 is expandable and contractible). The blood discharge assembly 82 further includes an outlet surge tank 94 which is also interconnected with the outlet manifold 90 and which allows the oxygenator system 10 to be operated in a manner which minimizes the generation of pressure pulses which can cause additional counterflows of blood through the oxygenator 14o In order to provide the operator with selective operating capabilities, however, a valve 98 is positioned between the outlet surge tank 94 and the outlet manifold 90 to again allow for a blood pressure pulse/counterflow operating mode as well.

The oxygenator 14 receives a preferably continuous flow of blood from the blood supply assembly 50 under laminar flow conditions (e.g., using a flow having a Reynolds Number less than about 2000) and oxygenates the same, as well as allows for the removal of carbon dioxide from the blood flow. Referring to both FIGS. 1 and 2, generally the oxygenator 14 includes a shell or housing 18 with a tube bundle 22 positioned therein. Oxygen inlet and outlet ports 34, 38, respectively, are positioned on the housing 18 to provide for a flow of oxygen through the oxygenator 14. In this regard, the oxygen supply assembly 106 includes an oxygen source 110 and oxygen inlet tubing 114 which interconnects the oxygen source 110 with the oxygen inlet port 34 on the housing 18 of the oxygenator 14. Consequently, the housing 18 functions as a conduit for the flow of oxygen through the oxygenator 14. Although the flow of oxygen is illustrated as being counter to the flow of blood, such is not required.

The tube bundle 22 is substantially contained within the housing 18 and includes a plurality of spaced and substantially axially or linearly extending tubes 26 which are retained between two vertically displaced headers 30, although other membrane configurations may be appropriate (e.g., tubes which are only generally axially extending, planar sheets, pleated sheets). The headers 30 are each configured (not shown) to allow for a flow of blood into and out of the tubes 26. Consequently, the tube bundle 22 is a conduit for the flow of blood through the oxygenator 14. Notwithstanding the illustration herein of the blood being contained within the tubes 26 of the tube bundle 22 and the oxygen within the housing 18, the reverse may be utilized whereby the oxygen is contained within the tubes 26 and the blood on the outside of the tubes 26 and within the housing 18, in which case the housing 18 and tube bundle 22 exterior form the conduit for the flow of blood through the oxygenator 14.

The tubes 26 of the tube bundle 22 each function as a membrane which allows for the mass transfer of oxygen into the blood and for the mass transfer of carbon dioxide out of the blood. That is, in a blood oxygenation application of the present invention the tubes 26 must be permeable at least to the diffusion of oxygen and carbon dioxide. In this regard, appropriate materials for the tubes 26 include microporous polypropylene and microporous polyethylene (possibly coated with silicone), and silicone rubber, with microporous polypropylene being preferred. Moreover, typically the wall thickness of the individual tubes 26 will range from about 10 microns to about 1,000 microns with an outer diameter being about 200 microns, and the density of the materials forming the tubes 26 will range from about 0.40 grams per cubic centimeter to about 1.30 grams per cubic centimeter. As a general range for all membrane oxygenators, about 20 microns to about 300 microns is a practical membrane thickness range. However, not only may different membrane configurations be utilized in practicing the present invention, but other properties/characteristics of the membrane may be tailored for a particular application and/or to meet specified performance criteria.

Due to the improvements in the oxygen mass transfer rate achievable in a blood oxygenation application of the present invention by a movement of the tubes 26 relative to the flow of blood therethrough, and specifically including the blood mass transfer boundary layer, the total surface area of the membranes or the tubes 26 which interfaces with the blood may be significantly reduced over existing commercial membrane blood oxygenators. This provides a number of benefits. Initially, this reduces the priming volume of the oxygenator 14. Moreover, for a given blood flow rate, the smaller the surface area of the membrane(s), the less total contact there is between the blood and the membrane(s). In one embodiment of the present invention, the total surface area of the tubes 26 which interfaces with the blood flow may be less than about 0.2 square meters for an infant unit and less than about 1.5 square meters for an adult unit, and is more preferably less than about 0.1 square meters for an infant unit and less than about 0.75 square meters for an adult unit. This can be contrasted with surfaces areas of about 0.4 square meters for typical prior art, infant oxygenators and about 3.0 square meters for typical prior art adult oxygenators. In one embodiment, the tube bundle 22 includes 41 tubes 26 which each have an inner diameter of about 0.1473 centimeters and a length of about 27.94 centimeters, although other membrane sizes and/or configurations may realize benefits associated with the present invention (e.g., the lengths of the blood channels may vary from about 1 centimeter to more than 30 centimeters).

As noted, the drive assembly 122 moves the tube bundle 22, particularly the individual tubes 26, relative to the flow of blood therethrough, and particularly the blood mass transfer boundary layer, to augment the mass transfer rate. The drive assembly 122 includes a drive unit 126 which in the illustrated embodiment axially reciprocates the tube bundle 22 between two positions. The drive unit 122 includes an axially reciprocable drive rod 130, a table 134 mounted on the upper end of the drive rod 130, and a support carriage 138 which appropriately engages the housing 18 of the oxygenator 14 to interconnect the same with the table 134. Consequently, vertical movement of the drive rod 130 and table 134 is transmitted to the vertically oriented oxygenator 14 to move the tube bundle 22 axially, and thereby the tubes 26, relative to the flow of blood therethrough, particularly the blood mass transfer boundary layer. Although vertical movement is described herein, other orientations may be appropriate for an axial reciprocation. Moreover, various other types of drive assemblies may be used.

In order to provide for a desired degree of control of the movement of the tube bundle 22 which controls the augmentation of mass transfer, the oxygenator system 10 includes a signal generator 142 which is interconnected with the drive unit 126. The signal generator 142 allows both the amplitude and frequency of driving signal provided to the drive unit 126 to be selected/adjusted, to thereby further control the movement of the tube bundle 22. That is, both the amplitude and frequency affect the improvements in the mass transfer rate associated with the present invention. Moreover, the signal generator 142 also allows for the provision of various types of wave forms to the drive unit 126 to alter the pattern of movement. For instance, a periodic and symmetrical signal such as sine wave may be utilized to control the axial reciprocation of the tube bundle 22, as well as a periodic and asymmetrical signal such as a saw tooth wave whereby the rate at which the tube bundle 22 is moved between the two extreme positions varies dependent upon the direction of travel of the tube bundle 22. In addition, a pause may be provided at one or both of the extreme positions or any intermediate position of the tube bundle 22 such that the tube bundle 22 is momentarily maintained in a substantially stationary position. The cumulative effect is that the operation of the oxygenator system 10 may be adapted, for instance, to the particular oxygenation needs of the blood flowing therethrough. It will be appreciated that other factors such as the concentration gradient (e.g., the partial pressure of oxygen in the gas), the blood flow rate, the blood hemoglobin concentration, the venous oxygen saturation, and the temperature of the blood also have an effect on mass transfer and may be selected/adjusted to meet the given oxygenation needs.

One particularly useful application for the oxygenator system 10 is in an extracorporeal circuit. In this case, both the blood reservoir 54 and the blood receptacle 102 would be a human being, although other intermediate processing-related equipment could be utilized. Nonetheless, in summarizing the operation of the oxygenator system 10, blood is provided by the blood supply assembly 50 to the oxygenator 14 where it flows through the individual tubes 26 of the tube bundle 22 and out through the blood discharge assembly 82. The flow of the blood through the oxygenator 14 is typically laminar (e.g., a Reynolds Number of typically less than about 2000) so as to reduce the potential for cell damage. Simultaneously with the flow of blood, oxygen (or air containing oxygen) from the oxygen supply assembly 106 flows through the housing 18, which in the illustrated embodiment is counter to the flow of the blood through the tubes 26. In order to improve upon the transfer of oxygen through the tubes 26 and into the blood, the oxygenator 14 in the illustrated embodiment is axially reciprocated by the drive assembly 122 to produce a relative movement between the tubes 2,5 and the blood flowing therethrough, and particularly the blood mass transfer boundary layer, to reduce the resistance to mass transfer in the blood mass transfer boundary layer.

The relative movement between the membrane and the blood mass transfer boundary layer is attributable in the illustrated embodiment to the use of the inlet and outlet bellows 42, 46, although it may be possible to achieve the desired degree of relative movement by utilizing only a single bellows (e.g., a bellows only on the inlet side, a bellows only on the outlet side). The bellows 42, 46 alternately expand (lengthen) and contract (shorten) to allow the oxygenator 14, particularly the tubes 26, to move not only relative to the flow of blood therethrough and specifically the blood mass transfer boundary layer, but relative to the substantially stationary inlet and outlet manifolds 66, 90. The bellows 42, 46 may thus be characterized as variable volume and/or variable length type connectors. Other connectors having these characteristics may also be appropriate, such as the slide, slip, or telescoping-like connector 170 illustrated in FIG. 1A. Generally, the connector 170 includes an inner tube 174 interconnected with one of the oxygenator 14 and the inlet/outlet manifold 66/90 depending upon whether it is on the inlet or outlet side of the oxygenator 14, and an outer tube 178 interconnected with the other of the oxygenator 14 and the inlet/outlet manifold 66/90. One or more lubricated sealing rings 182 are positioned between the inner tube 174 and outer tube 178 and are fixed relative to one of the tubes and slidable relative to the other such that the length and volume of the connector 170 may increase and decrease as dictated by the movement of the membrane.

By lengthening and/or increasing in volume during downward movement of the tube bundle 22, the outlet bellows 46 also effectively allows for an instantaneous increase in the flow out of the tube bundle 22 in comparison with a stationary tube bundle 22 since there is an increase in the relative velocity between the blood and particularly the blood mass transfer boundary layer and the tube bundle 22. This further characterizes the relative movement between the membrane and blood mass transfer boundary layer associated with the present invention.

Figure 3:
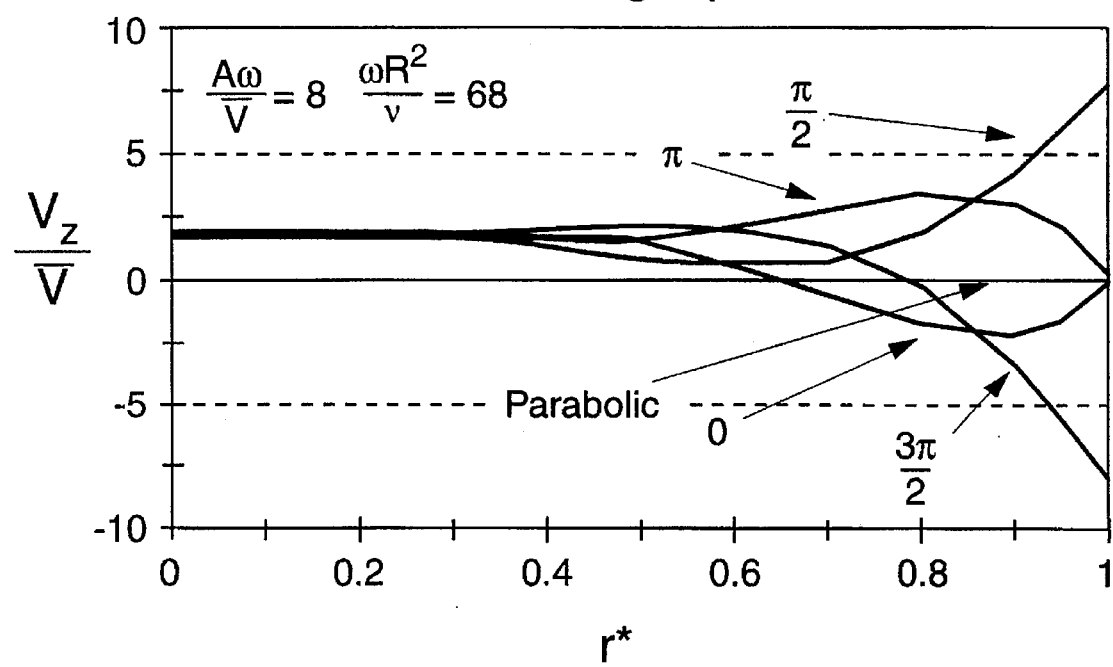
FIG. 3 illustrates the velocity profile in a tubular membrane oscillated in accordance with principles of the present invention.

The relative movement required and realized by the present invention is illustrated/supported by the graph of FIG. 3 which is generally the change in dimensionless fluid velocity along the radius of a tube 26 ("0" on the horizontal axis coinciding with the center of the tube 26 and "1" on the horizontal axis being at its wall). More specifically, FIG. 3 is a plot of the predicted axial velocity of the flow divided by the average velocity of the flow taken from the center of a tube 26 to its wall along a radius. This illustrates the effect which the above-described movements of the tube bundle 22, and thus the individual tubes 26, have on the velocity profile. Summarily, the above-described types of movement concentrate the effects on the blood in the blood mass transfer boundary region (which is again adjacent to the membrane), and have little if any effect on the more interiorly positioned portions of the flow. This maximizes the effects of the membrane movement.

Initially, in generating FIG. 3 via analytical solution, the oxygenator system 10 was assumed to operate such that $A\omega/\overline{V}$ was equal to 8 (where A is the one-half peak to peak amplitude of oscillation, $\omega$ is the angular frequency of oscillation, and $\overline{V}$ is the mean fluid velocity without vibrations), and $\omega R^2/\nu$ was equal to 68 (where R is the inner radius of the tube 26 and $\nu$ is the kinematic viscosity) since it was determined that mass transfer beneficiation was recorded with these values when moving the tubes 26 relative to the flow of liquid therethrough in companion studies.

Five curves are presented in FIG. 3. Four of the labeled curves are for different values of $\omega t$ in oscillating the tube 26 with a sinusoidal wave, whereas the fifth curve labeled "parabolic" illustrates the velocity profile within the tube 26 without wall oscillations. As can be seen, the movement of the tube bundle 22 and thus the: individual tubes 26 has a significant effect on the velocity at or adjacent to the wall of the tube 26, and has little or no effect on velocity profile at the "interior" portion of the flow. That is, the effects of the movement of the tube 26 occur primarily at a distance from the center of about 0.7 to 1 (zero again being the center of the tube 26 and 1 being its wall).

The above-described results realized by the present invention are important in that the blood mass transfer boundary layer exists adjacent to the wall of the tube 26. This blood mass transfer boundary layer provides a resistance to the mass transfer between the blood flow in the tubes 26 and the oxygen. Without movement of the tube bundle 22 in accordance with principles of the present invention, the slow moving blood near the wall of the tubes 26 becomes highly enriched in oxygen whereas the highest blood velocities are located further from the wall of the tubes 26. This causes a low mass transfer rate. By moving the tubes 26 relative to the flow of blood therethrough, and specifically by providing a large increase in relative velocity between the tubes 26 and blood mass transfer boundary layer, this significantly affects the concentration profiles and decreases the thickness of the blood mass transfer boundary layer (e.g., by increasing or steepening the oxygen concentration gradient within the blood mass transfer boundary layer) and thereby significantly augments the mass transfer rate As noted, the present invention requires a relative movement between the membrane and the blood mass transfer boundary layer, one type of which is produced by an axial reciprocation as discussed with regard to the system 10. In this case, the axial reciprocating motion of the tubes 26 relative to the flow of blood therethrough and particularly the blood mass transfer boundary layer in accordance with these principles may be further characterized by the effect which this type of motion has on the flow of blood. Initially, the axial reciprocation of the axially-extending tubes 26 itself induces substantially only a shear-like force between the flow of blood and the inner walls of the tubes 26. Moreover, the axial reciprocation of the axially-extending tubes 26 does not expose the blood to any centrifugal forces. Furthermore, the axial movement of the tubes 26 alone does not produce any significant secondary flows (i.e., flows which promote a mixing of the blood mass transfer boundary layer with more interiorly positioned portions of the flow). As will be discussed below, these characterizations of the effects in addition to the required relative movement which are achieved by the axial movement of the tube bundle 22 may not apply when utilizing other types of membrane movement also in accordance with principles of the present invention or when used in conjunction with passive augmentation techniques. It should be appreciated that the effects of the required relative movement of the present invention when utilizing different types of membrane configurations and/or types of movements (e.g., rotationally oscillating) may in fact enhance the benefits realized by the present invention.

Figure 13A:
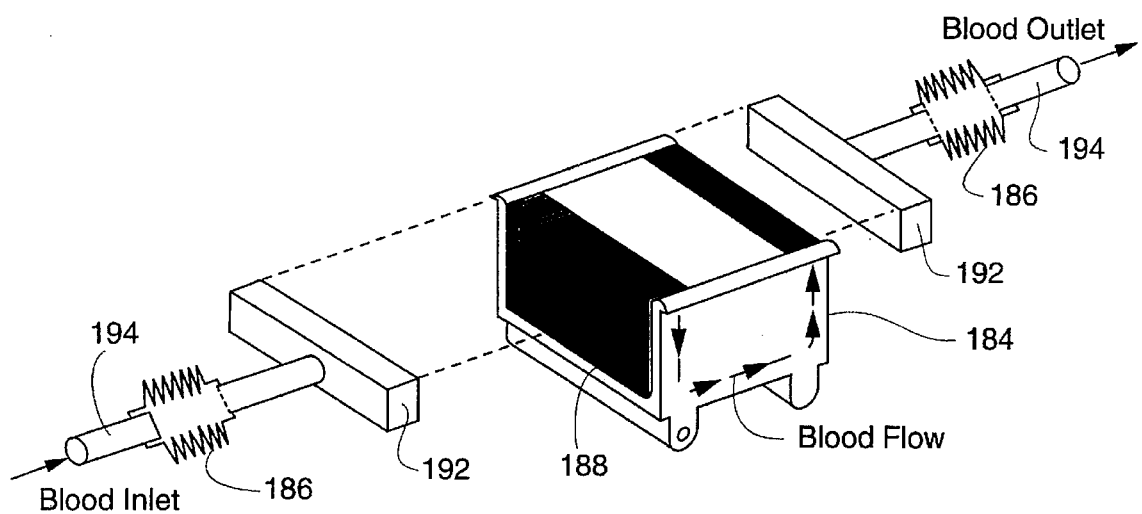
FIGS. 13A–B illustrate other membrane configurations which may utilize principles of the present invention.

With further regard to these other types of membrane configurations and/or movements, an axial-like motion could be used for a pleated sheet membrane oxygenator 184 as illustrated in FIG. 13A and discussed in more detail below. Moreover, axial-like movements may be used for tubular membrane oxygenators in which the tubes are only generally linearly extending. In this case, the tube bundle could remain axially extending and thus have a central, longitudinal axis. Instead of linear or axial tubes 26 as presented above, however, the tubes forming this tube bundle have a degree of curvature along one or more portions of their respective lengths (e.g., the individual tubes meander to a degree). The amount of curvature may be relatively small such that the tubes would remain effectively axially extending. In this case, although an axial reciprocation of these types of tubes would not produce only shear forces between the blood flow and the tubes, the primary force vector at any specific location which defines in part the resultant force would be in the same direction as the flow of blood therethrough to induce a shear-like action.

Figure 13B:
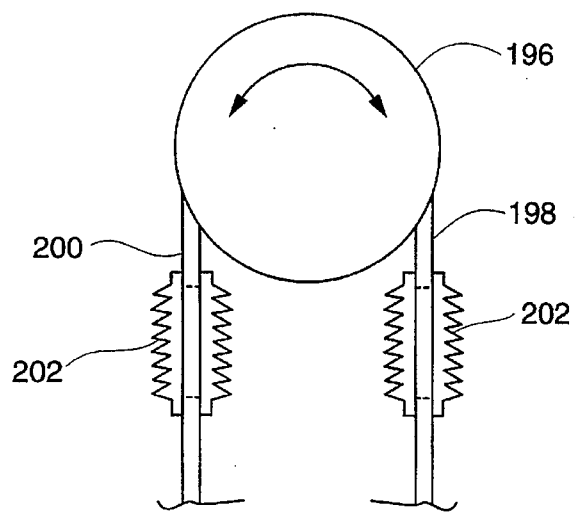

Other types of membrane movements may be utilized to realize the relative movement between the membrane and the mass transfer boundary layer adjacent thereto required by the present invention. For instance, rotational motion may be used. In FIG. 13B, a schematically depicted oxygenator 196 (e.g., a torroidal configuration) has its inlet 198 and outlet 200 interconnected with the above-described types of connectors 202 (e.g., variable volume, variable length), such that an oscillating, rotary-like movement may be utilized. Consequently, existing oscillating torroidal oxygenators may incorporate the types of connectors disclosed herein (e.g., bellows, telescoping) to realize the relative movement required by the present invention. In this case, there would not only be shear forces, but centrifugal forces as well. Moreover, secondary flows would be generated by the torroidal configuration. Consequently, the effects of movement of the membrane relative to the blood mass transfer boundary layer may be different than in the case of an axial reciprocation of an axial tube. These different effects, however, may further enhance the augmentation in the mass transfer rate attributed to movements in accordance with the present invention.

Although significant increases in the mass transfer rate may be realized by movement of the intermediate membrane in accordance with principles of the present invention, further increases in the mass transfer rate may be realized by pulsing the flow of fluid by the membrane and/or utilizing a fluid counterflow. For instance, in the blood oxygenator application and for the oxygenator system 10 of FIG. 1, the inlet and/or outlet surge tanks 70, 94 may be isolated from the oxygenator 14 by closing the valves 74, 98. This produces a pulsing of the flow of blood therethrough, and in one instance actually a counterflow (i.e., a flow of blood in substantially the opposite direction of the main direction of the flow). For instance, during upward movement of the tube bundle 22 and with the valve 98 being closed, there will is a corresponding pressure increase on the discharge end of the oxygenator 14 which will momentarily reduce the upward velocity of a portion of the blood flow somewhat, thereby increasing the velocity of the tubes 26 relative to the adjacent blood flow. Similarly, on subsequent downward movement of the tube bundle 22 and with the valve 74 closed, there will be a pressure increase on the inlet side of the oxygenator 14 which sends a pressure pulse of blood flow (e.g., it momentarily accelerates a portion of the blood flow) toward the discharge end of the oxygenator 14. These types of movement of the tubes 26 relative to the blood therein further disrupts the blood mass transfer boundary layer and improves the mass transfer rate. However, as noted the valves 74, 98 may be opened such that during axial reciprocation of the tube bundle 22, the generation of pressure pulses which may cause counterflows is minimized.

Although the above-noted pressure pulses and/or counterflows may be established by closure of the valves 74, 98, it will be appreciated that various dam-like structures or flow impediments may be positioned in the blood flow path, preferably more proximate the oxygenator 14 to increase the magnitude of the pulse/counterflow. For instance and referring to FIG. 4A, a circular disk 158 of a smaller diameter than the corresponding conduit may be perpendicularly positioned in the flow path of the blood into and/or out of the oxygenator 14. Moreover, and as illustrated in FIG. 4B, this circular disk 158 may be positioned in an inclined relationship relative to the walls defining the conduit. Moreover, and as illustrated in FIG. 4C, a circular disk 162 with a plurality of holes extending therethrough may also be utilized Notwithstanding these specific examples, it will be appreciated that generally a degree of a pressure pulse which causes additional counterflow may be achieved by positioning these such dam-like structures or flow impediments in any non-parallel relationship with the direction of the flow Moreover, it will be appreciated that using a flow impediment only on the inlet or outlet side may provide the desired degree of additional enhanced augmentation in the mass transfer rate.

In summary, the present invention requires that there be relative movement between the membrane and at least one mass transfer boundary layer adjacent thereto in order to reduce the resistance to mass transfer of the same. This relative movement may be affected by membrane movements other than axial as described herein and as noted above Moreover, oxygenator designs having membrane configurations other than tubular may also be utilized as noted above. For instance, relative movement between the membrane and blood mass transfer boundary layer may be achieved in a pleated membrane sheet oxygenator such as those disclosed in U.S. Pat. No. 4,663,125, issued May 5, 1987 to Gordon et al., and entitled "Membrane Medical Device", U.S. Pat. No. 4,455,230, issued Jun. 19, 1994 to Elgas et al., and entitled "Pleated Membrane Transfer Device Utilizing Potting and Thixotropic Adhesive", and U.S. patent application Ser. No. 970,781, filed Nov. 3, 1992, and entitled "Exchanger and Method for Manufacturing the Same", the entire disclosures of which are incorporated by reference in their entirety herein. Generally and again referring to FIG. 13A, in the pleated sheet membrane oxygenator 184, the above-described types of connectors 186 interconnect the inlet and outlet manifolds 192 of the oxygenator 184 with an appropriate tubing conduit 194. As such, an axial reciprocation of the oxygenator 184 is employed (drive assembly not shown) such that there would be relative movement between the pleated sheet(s) 188 which define the blood channel(s) and the blood mass transfer boundary layer adjacent thereto (e.g., an axial reciprocation along the direction of the apices of the pleats in which the blood flows in this same general direction). Moreover, relative movement between the membrane and blood mass transfer boundary layer may be achieved in a flat membrane sheet oxygenator (e.g., axial reciprocation parallel with the direction of the sheet). In addition and referring to FIG. 13B an oscillatory-like motion may be utilized for an oxygenator 184 as noted above.

Principles of the present invention are further illustrated by the following example:

EXAMPLE 1

Oxygenation of water with the above-noted oxygenator system 10 of FIG. 1 was used to demonstrate principles of the present invention. Generally, the augmentation in mass transfer associated with the present invention may be expressed as the ratio of the fluid Sherwood number with movement of the membrane in accordance with principles of the present invention ("$Sh_{fv}$") to the fluid Sherwood number using the same membrane but maintaining such in a stationary position ("$Sh_f$"). The fluid Sherwood number is a non-dimensional mass-transfer coefficient which can be correlated by the dimensionless groups $A\omega/V$ (the ratio of the one-half peak-to-peak vibrational velocity of the tube wall to the mean fluid velocity), $\omega R^2/\nu$ (the ratio of the characteristic time scale for momentum transport to the characteristic time scale for an oscillation cycle), Sc (the Schmidt number, the ratio of the characteristic time for mass transport via molecular diffusion to the characteristic time for momentum transport via viscous transfer), and Gz (the Graetz number, a dimensionless inverse contact time for mass transfer), With regard to the first dimensionless group, namely $A\omega/\overline{V}$ where A is the one half peak-to-peak amplitude of oscillation, $\omega$ is the angular frequency of oscillation, and $\overline{V}$ is the mean fluid velocity, the larger the value of this dimensionless group, the larger the value of the pulsation velocity to the mean velocity. For a given Schmidt and Graetz number and a fixed value for $\omega R^2/v$, there is an optimum value for this first dimensionless group since at the extremes there are no benefits in the mass transfer rate realized by movement of the tubes 26. That is, for an angular frequency of zero, there can of course be no increase in the mass transfer rate due to movement of the tubes 26 since they are in fact not moving. Moreover, for an infinite angular frequency, the movements of the tubes 26 are so fast that it is though there is no movement of the tubes 26 at all.

With regard to the second dimensionless group, namely $\omega R^2/v$, where is again the angular frequency of oscillation, R is the radius of the tube 26, and v is the kinematic viscosity of the flow, the larger value of this dimensionless group, the larger is the ratio of the characteristic time for the tube wall movement to be felt in the bulk of the flow relative to the characteristic time for a tube wall pulsation. For a given Schmidt and Graetz number and a fixed value for $A\omega/\overline{V}$, there is an optimum value for this second dimensionless group since at the extremes there are no benefits in the mass transfer rate realized by movement of the tubes 26. For instance, if this second dimensionless group is zero, the time required for molecular transport is zero, and thereby movement of the tubes 26 relative to the flow can have no benefit. Moreover, if this second dimensionless group is infinite which means that it takes an infinite time for molecular transport of momentum to occur, movement of the tubes 26 relative to the flow can have no effect on the mass transfer rate.

The Schmidt number is defined by the following equation: $Sc=v/D_L=(R^2/D_L)/R^2/v$, where $D_L$ is the liquid-phase diffusion coefficient for oxygen in water. The Schmidt number is the ratio of the time required for viscous or molecular diffusion of mass to the time required for molecular diffusion of momentum. Generally, the higher the Schmidt number, the greater realization of augmentation in the mass transfer rate due to movement of the tubes 26 relative to the flow therethrough.

The Graetz number is defined by the following equation: $Gz=Pe(\pi R/2L)$, where Pe is the Peclet number which is $\overline{V}RR/D_L$ and L is length of a tube 26. Generally, the Graetz number is effectively an inverse dimensionless contact time for mass transfer. The larger the Graetz number, the shorter the contact time between the blood and the oxygen in an oxygenation application. For the oxygenator 10, there is an optimum Graetz number for a given set of conditions. For instance, if the Graetz number is zero there is no flow and thus there is an infinite contact time is available for mass transfer, whereas if the Graetz number is infinite the contact time is zero. In either case, movement of the tubes 26 relative to the flow of blood therethrough cannot have any effect on the mass transfer rate. As such since movement of the tubes 26 relative to the flow of blood therethrough has no effect on the mass transfer rate at the extremes, there is an optimum between these extremes for a given set of conditions. However, the optimum Graetz number was not investigated in this study.

The ranges of parameters, which were investigated experimentally are presented in Table 1 below:

TABLE 1

| Range of Parameters | |
|---|---|
| Parameter | Range |
| Gz | 24–28 |
| $A\omega/\overline{V}$ | 4–16 |
| $\omega R^2/v$ | 10–65 |
| f | 6–18 Hz |
| 2A | 0.5 mm–12 mm |

Generally, the values of the parameters in Table 1 were systematically varied throughout the range of interest. The first set of results presented herein are those for which the $A\omega/\overline{V}$ parameter was held constant, while the $\omega R^2/v$ grouping was varied. Next, the results of experiments for which $\omega R^2/v$ was held constant and $A\omega/\overline{V}$ was varied are presented herein. By way of initial summary and as will be detailed herein, there was an increase in oxygen mass transfer when wall oscillations were imparted to the tube bundle 22. Moreover, for a given amplitude (as well as fluid and flow rate/velocity), there appears to be an optimum frequency or range of frequencies, and vice versa.

Figure 5:
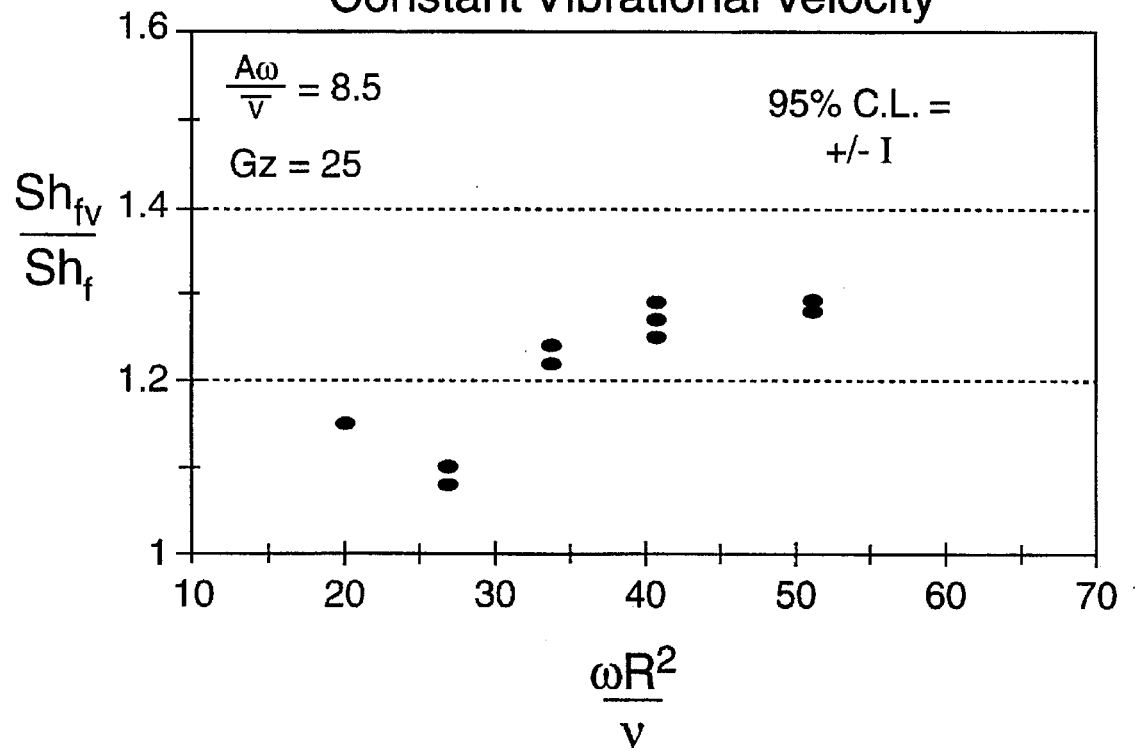
FIGS. 5–12 illustrate results of testing of principles of the present invention as presented in Example 1.
Figure 6:
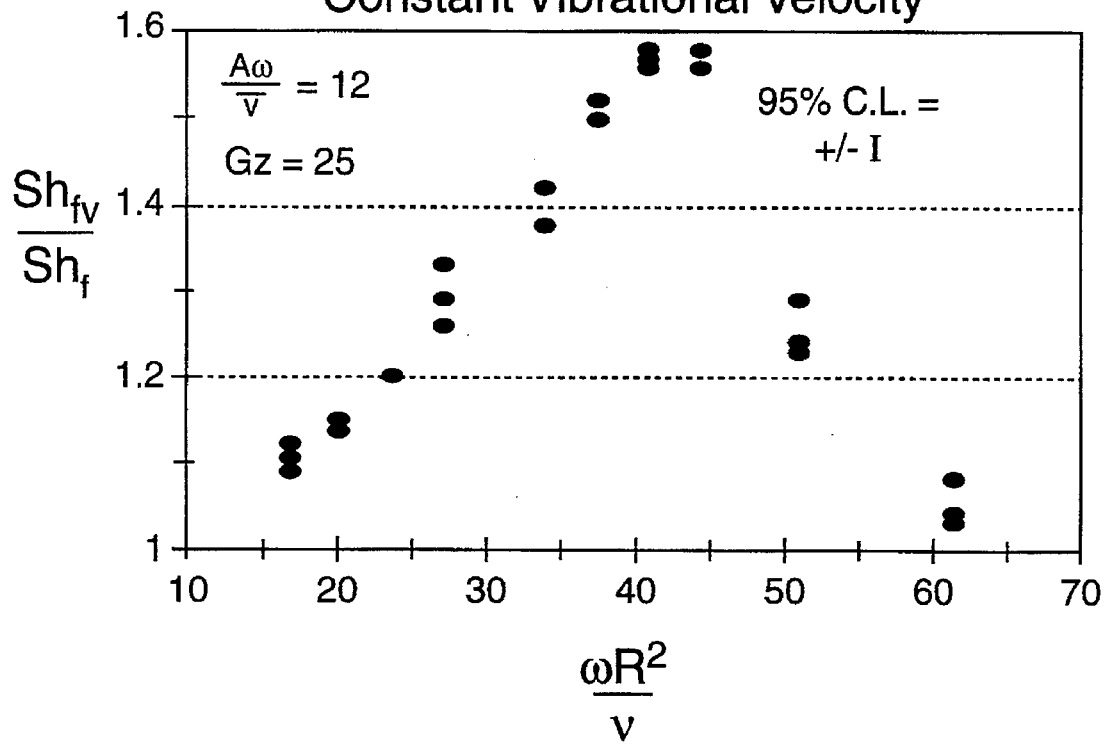
Figure 7:
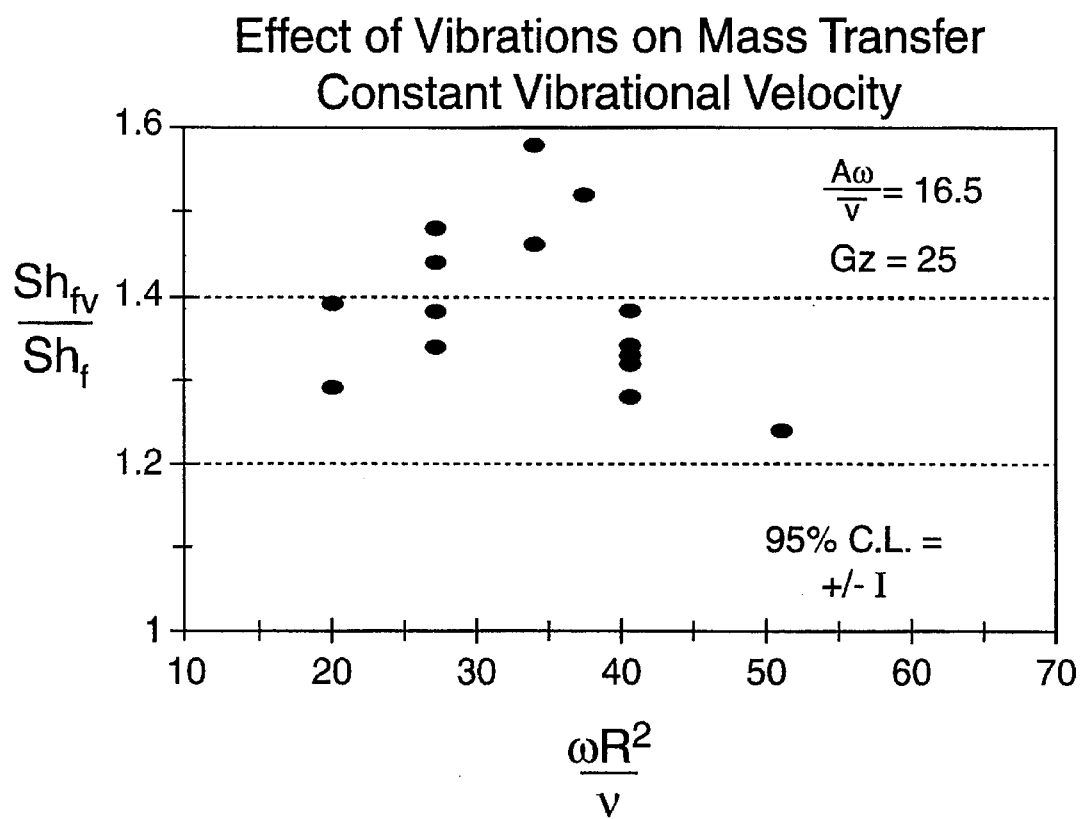

FIGS. 5–7 present the mass-transfer results from experiments in which $A\omega/\overline{V}$ was set at 8.5, 12, and 16.5, respectively, and $\omega R^2/v$ was varied, from 14–61. The level of mass-transfer augmentation was represented by the ratio of the Sherwood number with vibrations (axial reciprocation) to the Sherwood number without vibrations When vibrations increase the oxygen mass transfer to the fluid, the Sherwood number ratio will increase above unity. When there is no effect of vibrations on the mass transfer, this ratio will equal unity.

At the lowest value of the vibrational velocity group tested, namely $A\omega/\overline{V}=8.5$, FIG. 5 shows that the Sherwood-number ratio slowly increases with increasing $\omega R^2/v$ and then attains a nearly constant value of 1.3 at $\omega R^2/v=51$. In FIG. 6, where $A\omega/\overline{V}=12$, the Sherwood-number ratio increases with increasing $\omega R^2/v$ to a maximum value of 1.58 at $\omega R^2/v=41$. Then the Sherwood-number ratio decreases to nearly unity at $\omega R^2/v=61$. At the highest value of the vibrational velocity group tested, namely $A\omega/\overline{V}=16.5$, FIG. 7 shows that the Sherwood-number ratio increases with increasing $\omega R^2/v$ to a maximum value of 1.55 at $\omega R^2/v=34$. The Sherwood-number ratio then decreases to a value of 1.22 at $\omega R^2/v=51$.

An F-test was applied to the standard deviations of the experimental data to determine if the variances could be pooled. The F-test (95% confidence level) showed that the variances in the experimental data were not statistically different and hence, the variances were pooled to provide a better estimate of the true variance. Using the pooled estimate of the variance, the 95% confidence level about the means was calculated as follows:

$$95\%\ C.L. = \pm t_{0.025,df} \times \frac{S_e}{\sqrt{n_e}}$$

where $S_e$ is the pooled standard deviation, $n_e$ is the number of observations, df is the degrees of freedom and $t_d$ is a t-distribution. Using this equation, the 95% confidence level was calculated at ±0.037. The magnitude of the 95% confidence level is shown on the plots of the experimental data.

The results of the experiments for which the vibrational penetration depth, $\omega R^2/v$ was held constant while the vibrational velocity, $A\omega/\overline{V}$, was varied are presented in FIGS.

Figure 8:
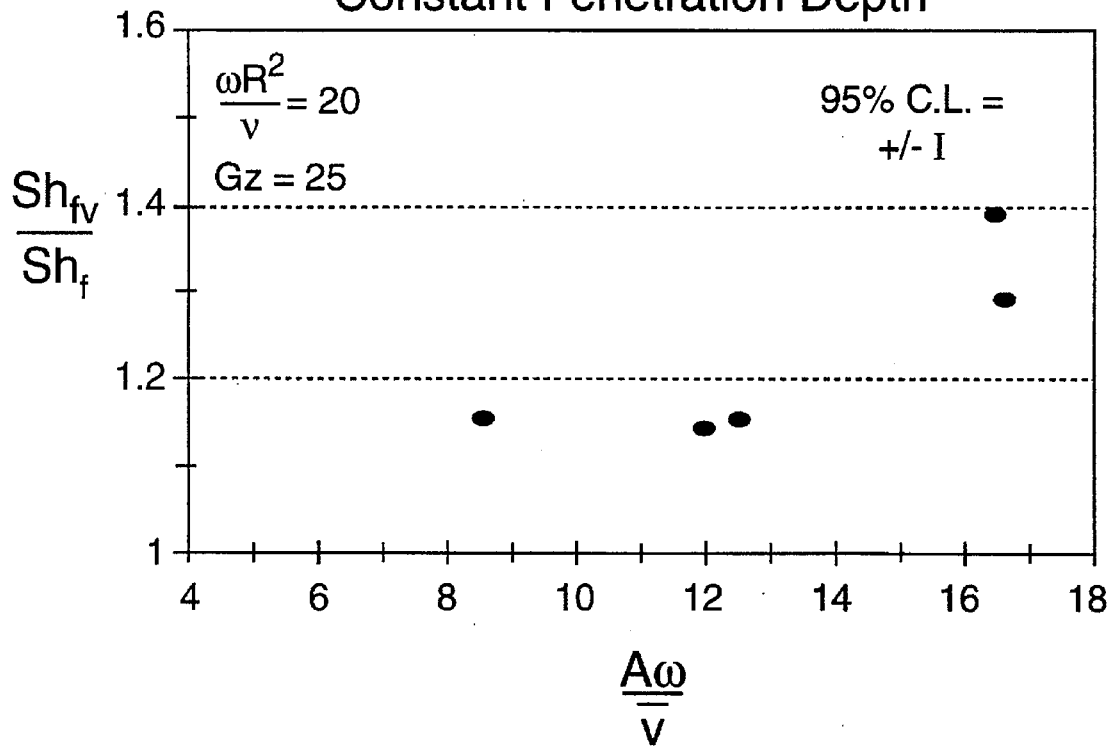
Figure 9:
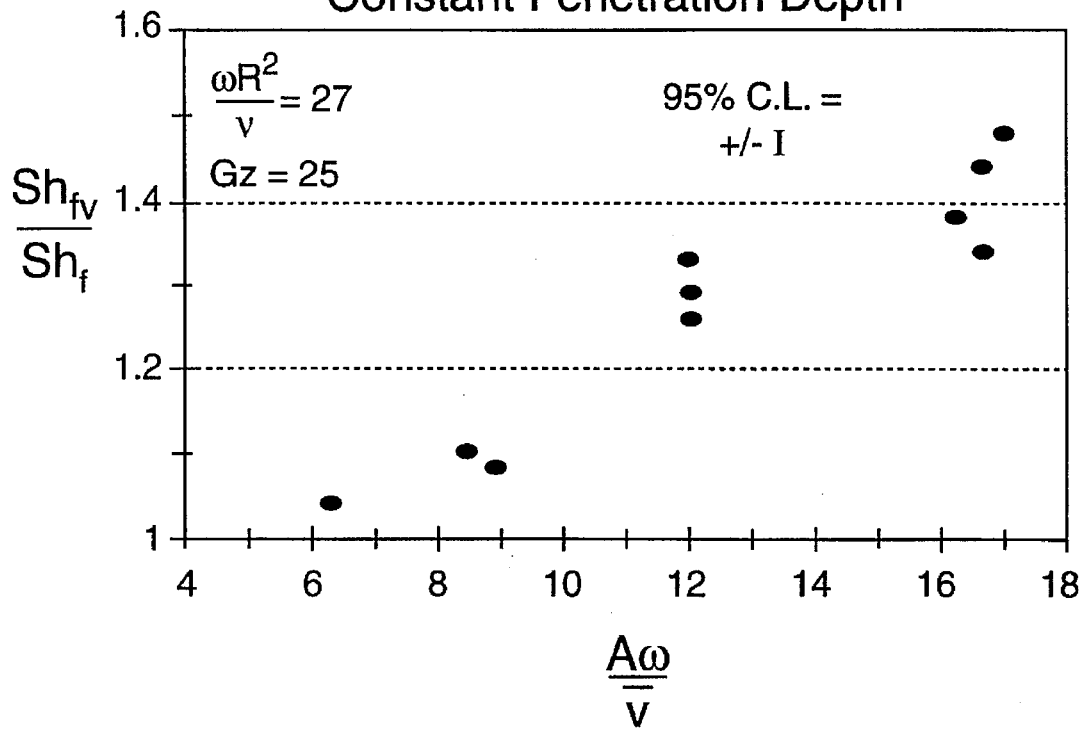
Figure 10:
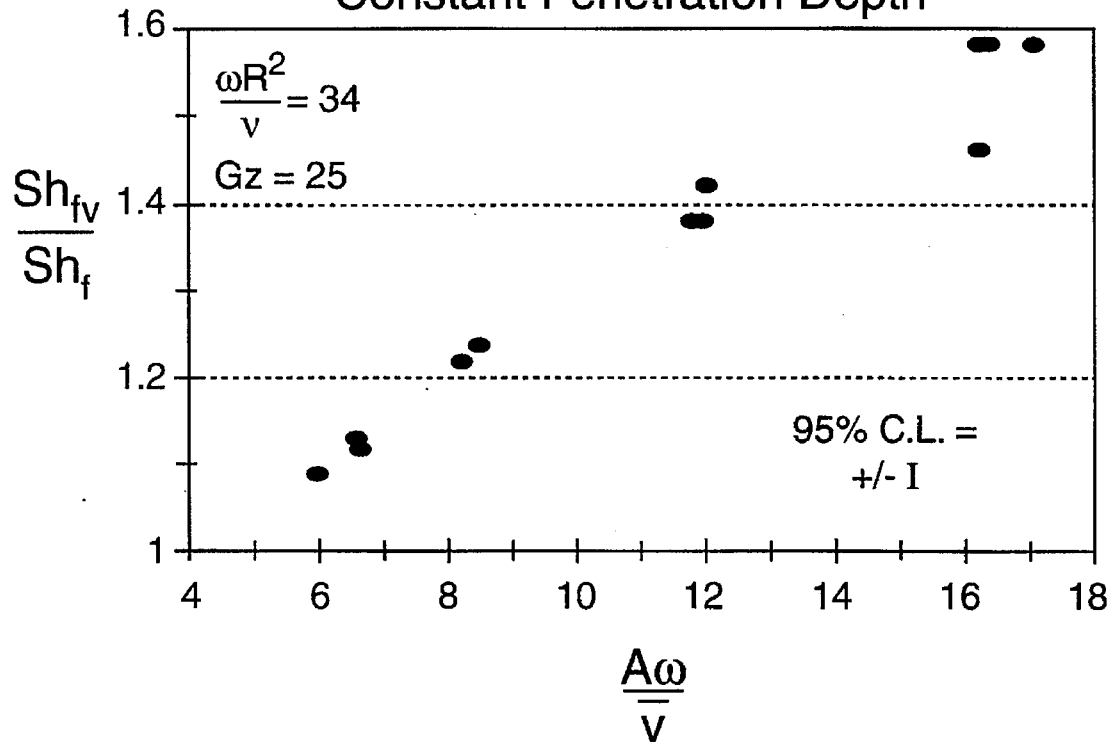
Figure 11:
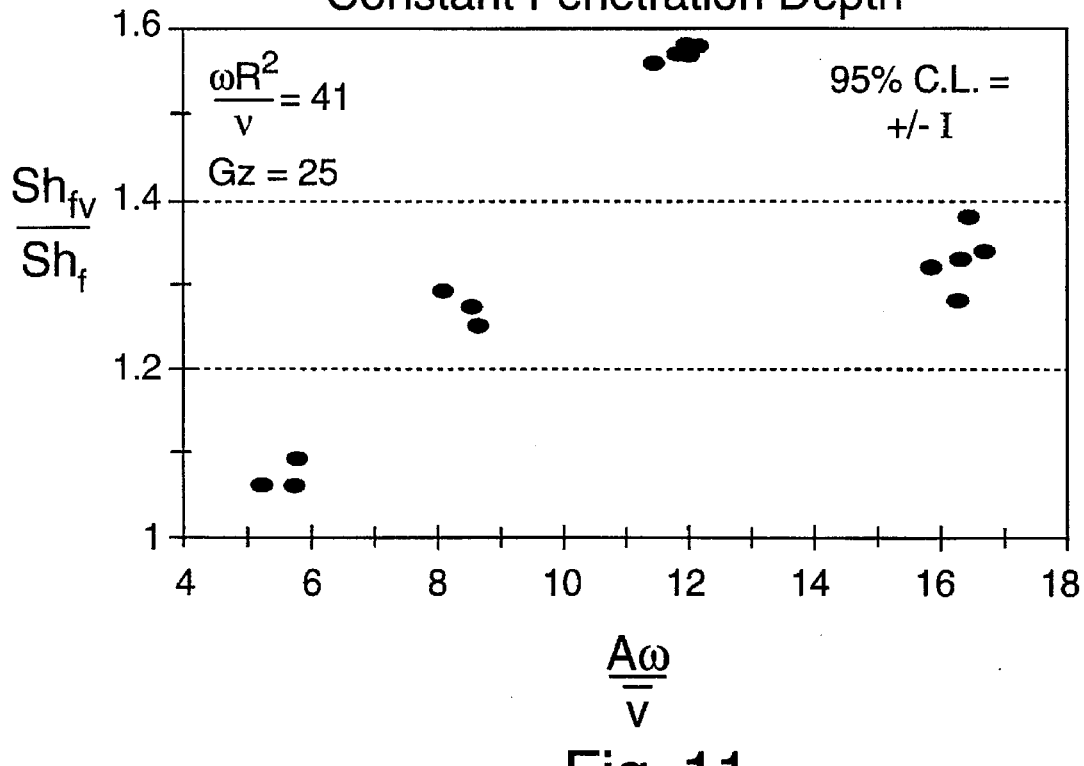
Figure 12:
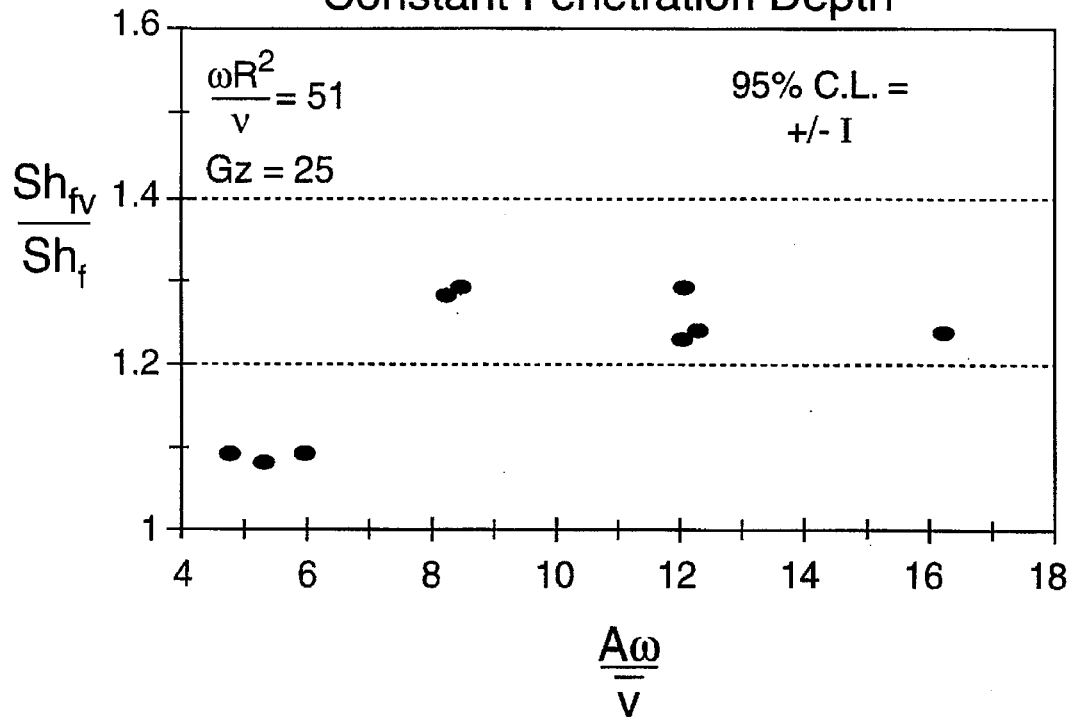

8–12. Notice in FIG. 8 that the Sherwood-number ratio remains at a constant value of 1.15 for values of the vibrational velocity group, $A\omega/\overline{V}$, between 8 and 12. However, above $A\omega/\overline{V}=12$, the mass-transfer augmentation increases slowly until a Sherwood-number ratio of 1.4 is reached at $A\omega/\overline{V}=16.5$. In FIG. 9, where $\omega R^2/\nu$ has been increased to $\omega R^2/\nu=27$, the Sherwood-number ratio increases with increasing $A\omega/\overline{V}$. The highest increase in mass transfer occurs at $A\omega/\overline{V}=16.5$, where the Sherwood-number ratio is equal to approximately 1.45. A similar trend is realized in FIG. 10, where $\omega R^2/\nu=34$. The Sherwood-number ratio increases with increasing vibrational velocity, until a value of 1.58 is reached at $A\omega/\overline{V}=16.5$. Note that the mass-transfer augmentation trend changes in FIG. 11. Here, the augmentation effect increases to a maximum Sherwood-number ratio of 1.59 at $A\omega/\overline{V}=12$. Beyond $A\omega/\overline{V}=12$, the augmentation effect decreases to a Sherwood number ratio of 1.35 at the highest vibrational velocity grouping value of $A\omega/\overline{V}=16.5$. And finally, FIG. 12 presents the augmentation effect for the highest value of the vibrational penetration depth group tested, namely $\omega R^2/\nu=51$. In this plot, the Sherwood-number ratio slowly increases with increasing vibrational velocity and then reaches a nearly constant value of 1.3 for values of $A\omega/\overline{V}$ greater than 8.5.

In order to determine if further mass-transfer augmentation could be realized by generating pressure pulses/counterflows counterflows in the tubes 26 of the tube bundle 22, several experiments were conducted for which the surge tanks 70, 94 were not utilized. That is, the valves 70, 94 were closed such that the above-described pressure pulses and/or counterflows exist in the tubes 26. Table 2 presents the values of the parameters that provided the maximum augmentation effect when the experimental apparatus was operated without surge tanks 70, 94. Notice that the maximum Sherwood-number ratio realized was equal to 2.65 for the Graetz number of 48.

TABLE 2

| Mass Transfer Data with Secondary Flows | | | |
|---|---|---|---|
| $Sh_{fv}/Sh_f$ | $A\omega/\overline{V}$ | $\omega R^2/\nu$ | Gz |
| 2.02 | 5.8 | 17 | 48 |
| 2.53 | 7.8 | 17 | 48 |
| 2.35 | 7.1 | 20 | 48 |
| 2.65 | 7.9 | 24 | 48 |
| 2.48 | 8.4 | 27 | 48 |
| 1.20 | 1.4 | 3.4 | 48 |
| 1.36 | 1.5 | 17 | 48 |
| 1.69 | 1.7 | 27 | 48 |
| 1.22 | 1.6 | 37 | 48 |

The data presented in Table 2 indicate that the mass-transfer performance of the tube bundle 22 was increased when the surge tanks 70, 94 were not utilized. That is and as discussed above, without the surge tanks 70, 94, the oscillations of the tube bundle 22 creates pressure pulsations that will produce an additional counterflow in the fluid. As the oxygenator is oscillated in the vertical direction, the pressure pulsation will increase the relative velocity between the individual tubes 26 and the flow therethrough, particularly the fluid adjacent thereto. This flow pattern will increase the relative velocity between the oscillating tubes 26 and the bulk fluid and therefore should increase the overall transfer of oxygen to the fluid.

Notice that for the highest mass-transfer enhancement listed in Table 2, $Sh_{fv}/Sh_f=2.65$, $A\omega/\overline{V}=7.9$ and $\omega R^2/\nu=24$ for Gz=48 (i.e., the optimum Graetz number again was not investigated). If this data point is superimposed onto FIG. 5, an interesting observation may be made The results with vibrations in the absence of the above-noted pressure pulses/counterflows indicate a maximum effect at a value of $\omega R^2/\nu=45$ or 50. Hence, the, effect with secondary flows could possibly increase the maximum enhancement to $Sh_{fv}/Sh_f=3.00$. The fact that the mass-transfer augmentation increases dramatically when pulses/counterflows are generated confirms that the performance of a device based upon wall oscillations could be improved by incorporating such flows into the system 14.

As shown in FIGS. 5, 6, and 7, imparting oscillations to the tubes 26 had the effect of increasing the oxygen mass transfer in the system 10. After analyzing the data for these plots, it appears that for a given value of $A\omega/\overline{V}$ there appears to be a value of $\omega R^2/\nu$ that optimizes the mass-transfer augmentation. Notice that in both FIGS. 6 and 7, the shape of the augmentation curves is similar except for the location of the maximum effect. It appears that the location of the peak augmentation shifts to lower values of $\omega R^2/\nu$ as $A\omega/\overline{V}$ increases to 16. A similar trend is evident in FIGS. 9–13. At the lower values of $\omega R^2/\nu$, as the vibrational velocity increases, the effect is to increase the mass-transfer augmentation in the system 10. However, above $\omega R^2/\nu=41$ the mass-transfer augmentation decreases with increased vibrational velocity.

EXAMPLE 2

In order to assess if the augmentation effect observed experimentally for oxygen transfer to water could also be realized for blood, several experiments were conducted using the same system 10 but employing blood in place of water. Stable inlet conditions were achieved by circulating a 2 liter aliquot of blood through a commercial blood oxygenator and adjusting the gas phase concentrations of oxygen, carbon dioxide, and nitrogen to achieve desired inlet blood oxygen saturations. Blood was then pumped from this toning circuit through the tube bundle 22. The gas phase of the tube bundle 22 was ventilated with pure oxygen.

Table 3 summarizes data from two separate experiments. In the first experiment, Samples 1 and 2 were obtained. For Sample 1, there were no oscillations. For Sample 2, the oscillation frequency was 15 Hertz and the oscillation amplitude was 0.159 inches. Without oscillations, the oxygen transfer rate was 0.507 cc/min., while with oscillations the oxygen transfer rate was 0.801 cc/min. The effect of the oscillations was to increase the oxygen transfer rate by 58%.

In the second experiment, Samples 3–9 were obtained. For Samples 3 and 4, there were no oscillations and the average oxygen transfer rate was 0.467 cc/min. For Sample 8, the oscillation frequency was 15 Hertz and the oscillation amplitude was 0.155 inches which resulted in an oxygen transfer rate of 0.934 cc/min. The effect of the oscillations was to increase the oxygen transfer rate by 100%. This same increase in oxygen transfer was achieved in Sample 9 with an oscillation frequency of 13 Hertz and an oscillation amplitude of 0.152 inches. The oscillation frequency and amplitude combinations used in Samples 5, 6, and 7 resulted in lower oxygen transfer rates than for Samples 8 and 9. However, the oxygen transfer rates for these samples were still significantly greater than for the samples with no oscillations.

TABLE 3

OXYGEN TRANSFER TO BLOOD IN AN OSCILLATING
MEMBRANE OXYGENATOR
Barometric Pressure = 630 mmHg, Temperature = 37° C.
Hemoglobin Concentration = 12.9 g/dL

| Sample Number | Blood Flowrate cc/min | Inlet Blood Oxygen Saturation % | Outlet Blood Oxygen Saturation % | Oscillation Frequency Hz | Oscillation Amplitude inches | Oxygen Transfer Rate cc/min |
|---|---|---|---|---|---|---|
| 1 | 23.5 | 65.2 | 77.6 | — | — | 0.507 |
| 2 | 23.5 | 66.5 | 86.0 | 15 | 0.159 | 0.801 |
| 3 | 23.2 | 60.7 | 72.0 | — | — | 0.457 |
| 4 | 23.2 | 59.5 | 71.3 | — | — | 0.477 |
| 5 | 23.2 | 61.0 | 77.6 | 15 | 0.095 | 0.671 |
| 6 | 23.2 | 59.3 | 77.6 | 15 | 0.122 | 0.740 |
| 7 | 23.9 | 59.0 | 76.2 | 17 | 0.085 | 0.716 |
| 8 | 23.9 | 59.5 | 81.9 | 15 | 0.155 | 0.934 |
| 9 | 23.9 | 60.2 | 82.6 | 13 | 0.152 | 0.934 |

The foregoing description of the present invention has been presented for purposes of illustration and description. For instance and as noted, the present invention may be used in medical device applications other than oxygenators. In the case where the present invention is incorporated into a dialyzer, there is both a blood mass transfer boundary layer and a dialysate mass transfer boundary layer which are of substantially equal resistance. In this case, relative movement may be provided between the membrane and each of the mass transfer boundary layers. However, the present invention only requires that there be relative movement between the membranes and at least one mass transfer boundary layer. As such, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method for affecting mass transfer between a fluid and blood, comprising the steps of:

separating a flow of blood and a flow of fluid with a membrane;

moving an entirety of said membrane relative to at least one mass transfer boundary layer associated with at least one of the flow of blood and the flow of fluid in a direction which is substantially parallel with a primary direction of at least one of the flow of blood and the flow of fluid; and transferring at least one component of at least one of the blood and the fluid through said membrane.

2. A method, as claimed in claim 1, wherein:

said moving step comprises using a symmetrical driving signal.

3. A method, as claimed in claim 1, wherein:

said moving step comprises using an asymmetrical driving signal.

4. A method, as claimed in claim 1, wherein:

said moving step comprises moving said membrane between first and second positions in a predetermined pattern comprising pausing for a predetermined period of time at least at one of said first position, said second position, and an intermediate position between said first and second positions.

5. A method, as claimed in claim 1, wherein:

said moving step comprises axially reciprocating said membrane between first and second positions.

6. A method, as claimed in claim 1, wherein:

said membrane defines at least a portion of a conduit for the flow of blood, wherein said method further comprises the step of at least one of increasing and decreasing the flow of blood out of said conduit during a least a portion of said moving step.

7. A method, as claimed in claim 6, wherein:

said increasing the flow step comprises increasing a volume of an outlet conduit connected to said conduit.

8. A method, as claimed in claim 1, further comprising the step of:

providing a counterflow of at least one of blood and fluid during at least a portion of said moving step.

9. A method, as claimed in claim 1, further comprising the steps of:

using an input signal to control said moving step; and selecting at least one of a wave form, an amplitude, and a frequency of said input signal.

10. A method, as claimed in claim 1, further comprising the step of:

generating substantially only shear forces between the mass transfer boundary layer and said membrane during said moving step.

11. A method, as claimed in claim 1, further comprising the step of:

reducing the resistance c,f the blood mass transfer boundary layer using substantially only said moving step.

12. A medical device for affecting mass transfer between blood and a fluid, comprising:

a housing;

at least one membrane disposed within said housing and having first and second sides, said membrane being permeable with respect to at least one component of at least one of the blood and the fluid;

a blood inlet fluidly interconnected with a space interfacing with said first side of said at least one membrane;

a fluid inlet fluidly interconnected with a space interfacing with said second side of said at least one membrane; and means for moving an entirety of said membrane, in a direction which is substantially parallel with a primary direction of at least one of said flow of blood and said flow of fluid, relative to at least one mass transfer boundary layer.

13. A device, as claimed in claim 12, wherein:

said at least one membrane comprises a substantially axially extending tube.

14. A device, as claimed in claim 12, further comprising:

a plurality of said membranes, wherein each said membrane comprises a substantially axially extending tube and wherein said plurality of tubes are disposed substantially parallel to each other, wherein one of said flow of blood and said flow of fluid is provided through said plurality of tubes and the other of said flow of blood and said flow of fluid is through at least a space between said plurality of tubes and said housing.

15. A device, as claimed in claim 14, wherein:

said plurality of tubes are spaced from each other, wherein said other of said flow of blood and said flow of fluid passes in a space between said tubes.

16. A device, as claimed in claim 12, wherein:

said at least one membrane is configured to provide for a substantially uniform flow of blood thereby having a flow field defined by substantially straight and parallel streamlines.

17. A device, as claimed in claim 12, wherein:

said at least one membrane comprises a substantially planar sheet.

18. A device, as claimed in claim 12, wherein:

said at least one membrane comprises a pleated sheet.

19. A device, as claimed in claim 12, wherein:

one of said blood inlet and said fluid inlet comprises an input manifold, said device further comprising:

a first variable volume connector positioned between and interconnecting a first end of said housing and said input manifold;

an output manifold; and a second variable volume connector positioned between and interconnecting a second end of said housing, opposite said first end, and said output manifold, wherein said at least one membrane is fixedly interconnected with said housing and wherein said means for moving said at least one membrane comprises said first and second variable volume connectors.

20. A device, as claimed in claim 19, wherein:

said first and second variable volume connectors each comprise a bellows.

21. A device, as claimed in claim 19, wherein:

said first and second variable volume connectors each comprise a telescoping connector.

22. A device, as claimed in claim 12, wherein:

the fluid comprises oxygen.

23. A device, as claimed in claim 12, wherein:

said means for moving comprises means for reciprocating said at least one membrane between first and second positions.

24. A device, as claimed in claim 1, further comprising:

means for driving said means for moving and means for selecting at least one of a wave form, a frequency, and an amplitude for said means for driving.

25. A device, as claimed in claim 12, further comprising:

means for driving said means for moving, said means for driving providing a symmetrical signal to said means for moving.

26. A device, as claimed in claim 12, further comprising:

means for driving said means for moving, said means for driving providing an asymmetrical signal to said means for moving.

27. A device, as claimed in claim 12, wherein:

said means for moving moves said at least one membrane between first and second positions, said device further comprising means for driving said means for moving, said means for driving causing said at least one membrane to pause for a predetermined period of time at least at one of said first position, said second position and an intermediate position between said first and second positions.

28. A device, as claimed in claim 12, further comprising:

an outlet conduit connected to said housing and fluidly connected with said flow of blood on said first side of said membrane, wherein said means for moving comprises means for accommodating at least one of an increase or a decrease in a magnitude of said flow of blood out of said housing during at least a portion of a movement of said at least one membrane provided by said means for moving.

29. A device, as claimed in claim 28, wherein:

said means for accommodating comprises a variable volume connector positioned between and interconnecting said outlet conduit and said housing.

30. A device, as claimed in claim 12, further comprising:

means for controlling an amount of mass transfer between the fluid and the blood.

31. A device, as claimed in claim 12, further comprising:

means for pulsing at least one of said flow of blood past said first side of said at least one membrane and said flow of fluid past said second side of said at least one membrane.

32. A device, as claimed in claim 12, further comprising:

means for passively augmenting the mass transfer between the blood and fluid.

33. A device, as claimed in claim 12, further comprising:

means for establishing a counterflow of blood on said first side of said at least one membrane.

34. A device, as claimed in claim 12, further comprising:

a substantially stationary inlet conduit;

first means for interconnecting said inlet conduit and said housing, said first means allowing said at least one membrane to move relative to said inlet conduit;

a substantially stationary outlet conduit; and second means for interconnecting said outlet conduit and said housing, said second means allowing said at least one membrane to move relative to said outlet conduit.

35. A device, as claimed in claim 12, further comprising:

at least one substantially stationary conduit; and means for interconnecting said stationary conduit and said housing, said means for interconnecting allowing said at least one membrane to move relative to said stationary conduit.

36. A device, as claimed in claim 35, further comprising:

means for establishing a counterflow of blood on said first side of said at least one membrane.

37. A device, as claimed in claim 36, wherein:

said means for establishing comprises at least one member positioned in said stationary conduit, said at least one member being disposed in a non-parallel position relative to a primary direction of said flow of blood past said first side of said at least one membrane.

38. A device, as claimed in claim 12, wherein:

said means for moving comprises means for generating substantially only a shear force between said at least one membrane and a portion of said flow of blood adjacent said at least one membrane.

39. A device, as claimed in claim 12, wherein:

said means for moving comprises first and second telescoping connectors interconnected with first and second ends of said housing, respectively.

40. A device, as claimed in claim 12, wherein:

said means for moving comprises at least one telescoping connector interconnected with said housing.

* * * * *